United States Patent [19]

Boss et al.

[11] Patent Number: 5,691,144
[45] Date of Patent: Nov. 25, 1997

US005691144A

[54] METHODS OF DETECTING NOVEL MUTATIONS RELATING TO X-LINKED CHARCOT-MARIE-TOOTH DISEASE

[75] Inventors: Michael Alan Boss, Arlington; Uma Ananth, Shrewsbury; Kimberley Ottaway, Belmont, all of Mass.

[73] Assignee: Athena Diagnostics, Inc., Worcester, Mass.

[21] Appl. No.: 658,469

[22] Filed: Jun. 5, 1996

[51] Int. Cl.$^6$ .............................. C12Q 1/68; C07H 21/04
[52] U.S. Cl. .......................... 435/6; 435/91.2; 536/23.1; 536/23.5; 536/24.31; 935/8; 935/77; 935/78; 436/63
[58] Field of Search ............................ 935/6, 8, 77, 78; 436/63; 536/23.1, 24.31, 23.5; 435/6, 91.2, 94

[56] References Cited

PUBLICATIONS

Bergoffen, J., et al., "Connexin Mutations in X–Linked Charcot–Marie–Tooth Disease", Science, 262:2039–2042 ( Dec. 24, 1993).
Bone, L.J., et al., "New Connexin32 Mutations Associated with X–Linked Charcot–Marie–Tooth Disease", Neurology, 45:1863–1866 (Oct. 1995).
Chance, P.F., and Fischbeck, K.H., "Molecular Genetics of Charcot–Marie–Tooth Disease and related Neuropathies", Human Molecular Genetics, 3:1503–1507 (1994).
Fairweather, N., et al., "Mutations in the Connexin32 Gene in X–Linked Dominant Charcot–Marie–Tooth Disease (CMTX1)", Human Molecular Genetics, 3(1):29–34 (1994).
Ionasesu, V., "Charcot–Marie–Tooth Neuropathies: From Clinical Description to Molecular Genetics", Muscle and Nerve, 18:267–275 (1995).
Ionasesu, V., et al., "New Point Mutations and Deletions of the Connexin32 Gene in X–Linked Charcot–Marie–Tooth Neuropathy", Neuromusc. Disord., 5(4):297–299 (1995).
Ionasescu, V., et al., "Point Mutations of the Connexin32 (GJB1) Gene in X–Linked Dominant Charcot–Marie–Tooth Neuropathy", Human Molecular Genetics, 3(2):355–358 (1994).
Kumar, N.M. and Gilula, N.A., "Coding for a Gap Junction Protein", The Journal of Cell Biology, 103:767–776 (Sep. 1986).
Orth, U., et al., "X–Linked Dominant Charcot–Marie–Tooth Neuropathy: Valine–38–Methionine Substitution of ConneXin32", Human Molecular Genetics, 3(9):1699–1700 (1994).
Tan, C.C., et al., "Novel Mutations in the Connexin32 Gene Associated with X–Linked Charcot–Marie–Tooth Disease", Human Mutation, 7:167–171 (1996).
Cherryson, A., et al., "Mutational Studies in X–Linked Charcot–Marie–Tooth Disease (CMTX)", Am. J. Hum. Genet., 55:Abstract No. 1261, A216 (1994).

Tan, C. and Ainsworth, P., "Novel Mutations in the connexin32 Gene Associated with X–linked Charcot–Marie–Tooth Disease", Am. J. Hum. Genet., 55:Abstract No. 1431, A245 (1994).
Nelis, E., et al., "Estimation of the Mutation Frequencies in Charcot–Marie–Tooth Disease Type 1 and Hereditary neuropathy with Liability to Pressure Palsies: A European Collaborative Study", Eur. J. Hum. Genet., 4:25–33 (1996).
Nelis, E., et al., "Mutation Analysis of the Connexin 32 (Cx32) gene in Charcot–Marie–Tooth Neuropathy Type 1: Identification of Five New Mutations", Human Mutation, 9:47–52 (1997).
Oterino, A., et al., "Arginine–164–tryptophan substitution in connexin32 associated with X linked dominant Charcot–Marie–Tooth disease", J. Med. Genet., 33:413–415 (1996).
Bruzzone, R., et al., "Null Mutations of connexin32 in Patients with X–Linked Charcot–Marie–Tooth Disease", Neuron., 13:1253–1260 (Nov., 1994).
Ionasescu, V.V., et al., "Mutations of the noncoding region of the connexin32 gene in X–linked dominant Charcot–Marie–Tooth neuropathy", Neurology, 47:541–544 (1996).
Pericak–Vance, M.A., et al., "Consortium Fine Localization of X–Linked Charcot–Marie–Tooth Disease (CMTX1): Additional Support that Conne xin32 Is the Defect in CMTX1", Hum. Hered, 45:121–128 (1995).
Ressot, C., et al., "X–linked dominant Chacot–Marie–Tooth neuropathy (CMTX): new mutations in the connexin32 gene", Hum. Genet., 98:172–175 (1996).

Primary Examiner—Stephanie W. Zitomer
Assistant Examiner—Debra Shoemaker
Attorney, Agent, or Firm—Hamilton, Brook, Smith & Reynolds, P.C.

[57] ABSTRACT

Specific mutations in the connexin-32 gene that are associated with X-linked Charcot-Marie-Tooth (CMT) disease are disclosed. Methods of diagnosing X-linked CMT disease are also disclosed. Methods include hybridization analysis, such as Southern or Northern analysis, which use hybridization of mutant connexin-32 nucleic acid probes to connexin-32 genes; direct mutation analysis by restriction digest; sequencing of the connexin-32 gene; hybridization of an allele-specific oligonucleotide with amplified genomic DNA; or identification of mutant connexin-32 proteins. Mutant connexin-32 nucleic acid probes are also disclosed. The mutant connexin-32 nucleic acid probes have a mutation in at least one of the following codons: 12, 26, 28, 44, 75, 86, 100, 103, 107, 124, 142, 154, 157, 160, 161, 172, 179, 181, 183, 185, 187, 198, 204, 205, 219, 230 and 235. Mutant connexin-32 nucleic acid probes having more than one of the mutations described above are also described, as are mutant connexin-32 nucleic acid probes having other mutations in addition to at least one mutation as described above. Isolated, mutant connexin-32 proteins encoded by mutant connexin-32 genes, as well as antibodies specific for the mutant connexin-32 proteins, are also disclosed.

15 Claims, 2 Drawing Sheets

```
CCTCTGGGAA AGGGCAGCAG GAGCCAGGTG TGGCAGTGAC AGGGAGGTGT GAATGAGGCA        60

GG ATG AAC TGG ACA GGT TTG TAC ACC TTG CTC AGT GGC GTG AAC CGG         107
   Met Asn Trp Thr Gly Leu Tyr Thr Leu Leu Ser Gly Val Asn Arg
    1           5                   10                  15

CAT TCT ACT GCC ATT GGC CGA GTA TGG CTC TCG GTC ATC TTC ATC TTC        155
His Ser Thr Ala Ile Gly Arg Val Trp Leu Ser Val Ile Phe Ile Phe
                20                  25                  30

AGA ATC ATG GTG CTG GTG GTG GCT GCA GAG AGT GTG TGG GGT GAT GAG        203
Arg Ile Met Val Leu Val Val Ala Ala Glu Ser Val Trp Gly Asp Glu
            35                  40                  45

AAA TCT TCC TTC ATC TGC AAC ACA CTC CAG CCT GGC TGC AAC AGC GTT        251
Lys Ser Ser Phe Ile Cys Asn Thr Leu Gln Pro Gly Cys Asn Ser Val
        50                  55                  60

TGC TAT GAC CAA TTC TTC CCC ATC TCC CAT GTG CGG CTG TGG TCC CTG        299
Cys Tyr Asp Gln Phe Phe Pro Ile Ser His Val Arg Leu Trp Ser Leu
    65                  70                  75

CAG CTC ATC CTA GTT TCC ACC CCA GCT CTC CTG GTG GCC ATG CAC GTG        347
Gln Leu Ile Leu Val Ser Thr Pro Ala Leu Leu Val Ala Met His Val
80                  85                  90                  95

GCT CAC CAG CAA CAC ATA GAG AAG AAA ATG CTA CGG CTT GAG GGC CAT        395
Ala His Gln Gln His Ile Glu Lys Lys Met Leu Arg Leu Glu Gly His
                100                 105                 110

GGG GAC CCC CTA CAC CTG GAG GAG GTG AAG AGG CAC AAG GTC CAC ATC        443
Gly Asp Pro Leu His Leu Glu Glu Val Lys Arg His Lys Val His Ile
            115                 120                 125

TCA GGG ACA CTG TGG TGG ACC TAT GTC ATC AGC GTG GTG TTC CGG CTG        491
Ser Gly Thr Leu Trp Trp Thr Tyr Val Ile Ser Val Val Phe Arg Leu
        130                 135                 140

TTG TTT GAG GCC GTC TTC ATG TAT GTC TTT TAT CTG CTC TAC CCT GGC        539
Leu Phe Glu Ala Val Phe Met Tyr Val Phe Tyr Leu Leu Tyr Pro Gly
    145                 150                 155

TAT GCC ATG GTG CGG CTG GTC AAG TGC GAC GTC TAC CCC TGC CCC AAC        587
Tyr Ala Met Val Arg Leu Val Lys Cys Asp Val Tyr Pro Cys Pro Asn
160                 165                 170                 175

ACA GTG GAC TGC TTC GTG TCC CGC CCC ACC GAG AAA ACC GTC TTC ACC        635
Thr Val Asp Cys Phe Val Ser Arg Pro Thr Glu Lys Thr Val Phe Thr
                180                 185                 190

GTC TTC ATG CTA GCT GCC TCT GGC ATC TGC ATC ATC CTC AAT GTG GCC        683
Val Phe Met Leu Ala Ala Ser Gly Ile Cys Ile Ile Leu Asn Val Ala
            195                 200                 205

GAG GTG GTG TAC CTC ATC ATC CGG GCC TGT GCC CGC CGA GCC CAG CGC        731
Glu Val Val Tyr Leu Ile Ile Arg Ala Cys Ala Arg Arg Ala Gln Arg
        210                 215                 220
```

FIGURE 1A

```
CGC TCC AAT CCA CCT TCC CGC AAG GGC TCG GGC TTC GGC CAC CGC CTC        779
Arg Ser Asn Pro Pro Ser Arg Lys Gly Ser Gly Phe Gly His Arg Leu
    225                 230                 235

TCA CCT GAA TAC AAG CAG AAT GAG ATC AAC AAG CTG CTG AGT GAG CAG        827
Ser Pro Glu Tyr Lys Gln Asn Glu Ile Asn Lys Leu Leu Ser Glu Gln
240                 245                 250                 255

GAT GGC TCC CTG AAA GAC ATA CTG CGC CGC AGC CCT GGC ACC GGG GCT        875
Asp Gly Ser Leu Lys Asp Ile Leu Arg Arg Ser Pro Gly Thr Gly Ala
                260                 265                 270

GGG CTG GCT GAA AAG AGC GAC CGC TGC TCG GCC TGC TGATGCCACA             921
Gly Leu Ala Glu Lys Ser Asp Arg Cys Ser Ala Cys
            275                 280

TACCAGGCAA CCTGCCATCC ATCCCCGACC CTGCCCTGGG C                          962
```

FIGURE 1B

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
( A ) LENGTH: 962 base pairs
( B ) TYPE: nucleic acid
( C ) STRANDEDNESS: double
( D ) TOPOLOGY: linear ( i i ) MOLECULE TYPE: DNA (genomic)

( i x ) FEATURE:
( A ) NAME/KEY: CDS
( B ) LOCATION: 63..911

( x i ) SEQUENCE DESCRIPTION: SEQ ID NO:1:

```
CCTCTGGGAA AGGGCAGCAG GAGCCAGGTG TGGCAGTGAC AGGGAGGTGT GAATGAGGCA            60

GG ATG AAC TGG ACA GGT TTG TAC ACC TTG CTC AGT GGC GTG AAC CGG             107
   Met Asn Trp Thr Gly Leu Tyr Thr Leu Leu Ser Gly Val Asn Arg
   1               5                   10                  15

CAT TCT ACT GCC ATT GGC CGA GTA TGG CTC TCG GTC ATC TTC ATC TTC            155
His Ser Thr Ala Ile Gly Arg Val Trp Leu Ser Val Ile Phe Ile Phe
                20                  25                  30

AGA ATC ATG GTG CTG GTG GTG GCT GCA GAG AGT GTG TGG GGT GAT GAG            203
Arg Ile Met Val Leu Val Val Ala Ala Glu Ser Val Trp Gly Asp Glu
            35                  40                  45

AAA TCT TCC TTC ATC TGC AAC ACA CTC CAG CCT GGC TGC AAC AGC GTT            251
Lys Ser Ser Phe Ile Cys Asn Thr Leu Gln Pro Gly Cys Asn Ser Val
        50                  55                  60

TGC TAT GAC CAA TTC TTC CCC ATC TCC CAT GTG CGG CTG TGG TCC CTG            299
Cys Tyr Asp Gln Phe Phe Pro Ile Ser His Val Arg Leu Trp Ser Leu
    65                  70                  75

CAG CTC ATC CTA GTT TCC ACC CCA GCT CTC CTC GTG GCC ATG CAC GTG            347
Gln Leu Ile Leu Val Ser Thr Pro Ala Leu Leu Val Ala Met His Val
80                  85                  90                  95

GCT CAC CAG CAA CAC ATA GAG AAG AAA ATG CTA CGG CTT GAG GGC CAT            395
Ala His Gln Gln His Ile Glu Lys Lys Met Leu Arg Leu Glu Gly His
                100                 105                 110

GGG GAC CCC CTA CAC CTG GAG GAG GTG AAG AGG CAC AAG GTC CAC ATC            443
Gly Asp Pro Leu His Leu Glu Glu Val Lys Arg His Lys Val His Ile
            115                 120                 125

TCA GGG ACA CTG TGG TGG ACC TAT GTC ATC AGC GTG GTG TTC CGG CTG            491
Ser Gly Thr Leu Trp Trp Thr Tyr Val Ile Ser Val Val Phe Arg Leu
        130                 135                 140

TTG TTT GAG GCC GTC TTC ATG TAT GTC TTT TAT CTG CTC TAC CCT GGC            539
Leu Phe Glu Ala Val Phe Met Tyr Val Phe Tyr Leu Leu Tyr Pro Gly
    145                 150                 155

TAT GCC ATG GTG CGG CTG GTC AAG TGC GAC GTC TAC CCC TGC CCC AAC            587
Tyr Ala Met Val Arg Leu Val Lys Cys Asp Val Tyr Pro Cys Pro Asn
160                 165                 170                 175

ACA GTG GAC TGC TTC GTG TCC CGC CCC ACC GAG AAA ACC GTC TTC ACC            635
Thr Val Asp Cys Phe Val Ser Arg Pro Thr Glu Lys Thr Val Phe Thr
                180                 185                 190

GTC TTC ATG CTA GCT GCC TCT GGC ATC TGC ATC ATC CTC AAT GTG GCC            683
Val Phe Met Leu Ala Ala Ser Gly Ile Cys Ile Ile Leu Asn Val Ala
            195                 200                 205

GAG GTG GTG TAC CTC ATC ATC CGG GCC TGT GCC CGC CGA GCC CAG CGC            731
Glu Val Val Tyr Leu Ile Ile Arg Ala Cys Ala Arg Arg Ala Gln Arg
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|                      |     |     |     | 210 |     |     |     |     |     | 215 |     |     |     |     | 220 |     |

```
CGC  TCC  AAT  CCA  CCT  TCC  CGC  AAG  GGC  TCG  GGC  TTC  GGC  CAC  CGC  CTC        779
Arg  Ser  Asn  Pro  Pro  Ser  Arg  Lys  Gly  Ser  Gly  Phe  Gly  His  Arg  Leu
     225                      230                      235

TCA  CCT  GAA  TAC  AAG  CAG  AAT  GAG  ATC  AAC  AAG  CTG  CTG  AGT  GAG  CAG        827
Ser  Pro  Glu  Tyr  Lys  Gln  Asn  Glu  Ile  Asn  Lys  Leu  Leu  Ser  Glu  Gln
240                           245                      250                      255

GAT  GGC  TCC  CTG  AAA  GAC  ATA  CTG  CGC  CGC  AGC  CCT  GGC  ACC  GGG  GCT        875
Asp  Gly  Ser  Leu  Lys  Asp  Ile  Leu  Arg  Arg  Ser  Pro  Gly  Thr  Gly  Ala
                    260                      265                      270

GGG  CTG  GCT  GAA  AAG  AGC  GAC  CGC  TGC  TCG  GCC  TGC  TGATGCCACA               921
Gly  Leu  Ala  Glu  Lys  Ser  Asp  Arg  Cys  Ser  Ala  Cys
               275                      280

TACCAGGCAA  CCTGCCATCC  ATCCCCGACC  CTGCCCTGGG  C                                    962
```

( 2 ) INFORMATION FOR SEQ ID NO:2:

( i ) SEQUENCE CHARACTERISTICS:
        ( A ) LENGTH: 283 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asn  Trp  Thr  Gly  Leu  Tyr  Thr  Leu  Leu  Ser  Gly  Val  Asn  Arg  His
1                   5                   10                      15

Ser  Thr  Ala  Ile  Gly  Arg  Val  Trp  Leu  Ser  Val  Ile  Phe  Ile  Phe  Arg
               20                  25                  30

Ile  Met  Val  Leu  Val  Val  Ala  Ala  Glu  Ser  Val  Trp  Gly  Asp  Glu  Lys
          35                  40                  45

Ser  Ser  Phe  Ile  Cys  Asn  Thr  Leu  Gln  Pro  Gly  Cys  Asn  Ser  Val  Cys
     50                  55                  60

Tyr  Asp  Gln  Phe  Phe  Pro  Ile  Ser  His  Val  Arg  Leu  Trp  Ser  Leu  Gln
65                  70                  75                              80

Leu  Ile  Leu  Val  Ser  Thr  Pro  Ala  Leu  Leu  Val  Ala  Met  His  Val  Ala
               85                  90                  95

His  Gln  Gln  His  Ile  Glu  Lys  Lys  Met  Leu  Arg  Leu  Glu  Gly  His  Gly
               100                 105                 110

Asp  Pro  Leu  His  Leu  Glu  Glu  Val  Lys  Arg  His  Lys  Val  His  Ile  Ser
          115                 120                 125

Gly  Thr  Leu  Trp  Trp  Thr  Tyr  Val  Ile  Ser  Val  Val  Phe  Arg  Leu  Leu
          130                 135                 140

Phe  Glu  Ala  Val  Phe  Met  Tyr  Val  Phe  Tyr  Leu  Leu  Tyr  Pro  Gly  Tyr
145                 150                 155                             160

Ala  Met  Val  Arg  Leu  Val  Lys  Cys  Asp  Val  Tyr  Pro  Cys  Pro  Asn  Thr
               165                 170                 175

Val  Asp  Cys  Phe  Val  Ser  Arg  Pro  Thr  Glu  Lys  Thr  Val  Phe  Thr  Val
          180                 185                 190

Phe  Met  Leu  Ala  Ala  Ser  Gly  Ile  Cys  Ile  Ile  Leu  Asn  Val  Ala  Glu
          195                 200                 205

Val  Val  Tyr  Leu  Ile  Ile  Arg  Ala  Cys  Ala  Arg  Arg  Ala  Gln  Arg  Arg
     210                 215                 220

Ser  Asn  Pro  Pro  Ser  Arg  Lys  Gly  Ser  Gly  Phe  Gly  His  Arg  Leu  Ser
225                 230                 235                             240

Pro  Glu  Tyr  Lys  Gln  Asn  Glu  Ile  Asn  Lys  Leu  Leu  Ser  Glu  Gln  Asp
                    245                 250                 255
```

-continued

```
Gly Ser Leu Lys Asp Ile Leu Arg Arg Ser Pro Gly Thr Gly Ala Gly
            260                 265                 270
Leu Ala Glu Lys Ser Asp Arg Cys Ser Ala Cys
            275                 280
```

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

TGAGGCAGGA TGAACTGGAC AGGT                        24

( 2 ) INFORMATION FOR SEQ ID NO:4:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TTGCTGGTGA GCCACGTGCA TGGC                        24

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

ATCTCCCATG TGCGGCTGTG GTCC                        24

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TGGCAGGTTG CCTGGTATGT                            20

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GATGATGAGG TACACCACCT                            20

( 2 ) INFORMATION FOR SEQ ID NO:8:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear (xi) SEQUENCE DESCRIPTION: SEQ ID NO:8:

CCGTCTTCAT GCTAGCTGCC TCTGG 25

METHODS OF DETECTING NOVEL MUTATIONS RELATING TO X-LINKED CHARCOT-MARIE-TOOTH DISEASE

BACKGROUND OF THE INVENTION

Charcot-Marie-Tooth (CMT) neuropathy, also known as hereditary motor and sensory neuropathy, is a heterogeneous group of inherited diseases of peripheral nerves. CMT is a common disorder affecting both children and adults, and causing significant neuromuscular impairment. It is estimated that 1/2500 persons have a form of CMT, making it one of the largest categories of genetic diseases.

CMT is traditionally classified by whether the primary pathological defect is degeneration of myelin (CMT1) or of axons (CMT2) in the peripheral nerves. CMT1 is a genetically heterogeneous group of chronic demyelinating polyneuropathies with loci mapping to chromosome 17 (CMT1A), chromosome 1 (CMT1B), the X chromosome (CMTX) and to another unknown autosome (CMT1C). CMT1A mutations are associated with the gene for peripheral myelin protein 22 (PMP22); CMT1B mutations are associated with myelin protein P zero ($P_0$); and CMTX mutations are associated with the connexin-32 gene (Cx32). Connexin-32 is a 32-kilodalton protein, located at uncompacted folds of schwann cell cytoplasm around the nodes of Ranvier and at Schmidt-Lanterman incisures. This localization suggests a role for gap junctions composed of connexin-32 in providing a pathway for the transfer of ions and nutrients across and around the myelin sheath.

The clinical features of CMTX include demyelinating neuropathy characterized by progressive distal extremity weakness, atrophy, sensory loss, and areflexia; absence of male-to-male transmission; and a generally earlier onset and faster rate of progression of illness in males. Distinguishing between CMT1A and CMTX based on clinical and family history, or results from motor nerve conduction velocity (NCV) testing, is extremely difficult. Complicating the clinical diagnosis further is the high rate of affected female carriers of the CMTX mutations: the CMTX family pedigrees therefore do not demonstrate an X-linked transmission pattern. CMTX may be present in any families without male-to-male transmission of the disease. Methods to distinguish CMTX from other forms of CMT disease are necessary to facilitate disease diagnosis and treatment.

SUMMARY OF THE INVENTION

The invention pertains to specific mutations in the connexin-32 gene that are associated with CMTX disease. The invention includes methods of diagnosing CMTX disease in an individual by detecting the presence of particular mutations associated with CMTX disease. The mutations associated with CMTX disease include mutations in the following codons of the connexin-32 gene: 26, 28, 44, 86, 100, 103, 107, 124, 154, 157, 160, 161, 179, 181, 183, 187, 198, 204, 205, 219, 230 and 235. The mutation can be the addition or subtraction of a single nucleotide in the codon, resulting in a frame shift mutation; the change of at least one nucleotide in the codon, resulting in a change in the amino acid encoded by the codon; the change of at least one nucleotide in the codon, resulting in a change of the codon to a stop codon; the deletion of all three nucleotides in the codon, resulting in a deletion of the amino acid encoded by the codon; or the change of at least one nucleotide in the codon, resulting in a synonymous codon mutation, in any of the above codons. Other mutations associated with CMTX disease include certain specific mutations in the above codons, as well as certain specific mutations in codons 12, 75, 142, 172 or 185. The specific mutations associated with CMTX disease include: a change in the nucleic acid sequence of codon 12 from GGC to GGT; a change in the nucleic acid sequence of codon 26 from TCG to TTG; a change in the nucleic acid sequence of codon 28 from ATC to AAC; a change in the nucleic acid sequence of codon 44 from TGG to TTG; a change in the nucleic acid sequence of codon 75 from CGG to TGG; a change in the nucleic acid sequence of codon 86 from ACC to TCC; a change in the nucleic acid sequence of codon 100 from CAC to TAC; a change in the nucleic acid sequence of codon 103 from AAG to GAG; a change in the nucleic acid sequence of codon 107 from CGG to TGG; a change in the nucleic acid sequence of codon 124 from AAG to AG; a change in the nucleic acid sequence of codon 142 from CGG to CAG; a change in the nucleic acid sequence of codon 154 from TAT to TAA; a change in the nucleic acid sequence of codon 157 from TAC to TGC; a change in the nucleic acid sequence of codon 160 from TAT to CAT; a change in the nucleic acid sequence of codon 161 from GCC to GCT; a change in the nucleic acid sequence of codon 172 from CCC to CTC; a change in the nucleic acid sequence of codon 179 from TGC to CGC; a change in the nucleic acid sequence of codon 181 from GTG to ATG; a change in the nucleic acid sequence of codon 183 from CGC to TGC; or a deletion of codon 185; a change in the nucleic acid sequence of codon 187 from AAA to GAA; a change in the nucleic acid sequence of codon 198 from TCT to TTT; a change in the nucleic acid sequence of codon 204 from CTC to GTC; a change in the nucleic acid sequence of codon 205 from AAT to AGT; a change in the nucleic acid sequence of codon 219 from CGC to TGC; a change in the nucleic acid sequence of codon 230 from CGC to TGC; and a change in the nucleic acid sequence of codon 235 from TTC to TGC.

The mutations associated with CMTX disease can be identified by numerous methods, such as Southern analysis of genomic DNA; direct mutation analysis by restriction enzyme digestion; Northern analysis of RNA; gene isolation and sequencing; hybridization of an allele-specific oligonucleotide with amplified gene products; or analysis of the connexin-32 protein. For example, a sample of DNA containing the connexin-32 gene is obtained from an individual suspected of having CMTX disease or of being a carrier for the disease (the test individual). The DNA is contacted with at least one mutant connexin-32 nucleic acid probe under conditions sufficient for specific hybridization of the connexin-32 gene to the mutant connexin-32 nucleic acid probe. The mutant connexin-32 nucleic acid probe comprises cDNA of the connexin-32 gene, or a fragment of the gene, having at least one of the mutations described above, or an RNA fragment corresponding to such a cDNA fragment. The presence of specific hybridization of the mutant connexin-32 nucleic acid fragment to the mutant connexin-32 nucleic acid probe is indicative of CMTX disease.

Alternatively, direct mutation analysis by restriction digest of a sample of DNA from the test individual can be conducted, if the mutation results in the creation or elimination of a restriction site. The digestion pattern of the relevant DNA fragment or fragments indicate(s) the presence or absence of the mutation associated with CMTX disease. The presence of a mutation associated with CMTX disease can also be diagnosed by sequence data. A sample of genomic DNA from the test individual is obtained, and the sequence of the connexin-32 gene, or a fragment of the gene, is determined. The sequence of the connexin-32 gene from the individual is compared with the known sequence of the connexin-32 gene. The presence of a mutation, as described above, in the connexin-32 gene of the individual is indicative of the CMTX disease. In addition, the presence of a mutation associated with CMTX disease can be diagnosed by dot-blot hybridization of an allele-specific oligonucleotide with amplified genomic DNA. A sample of genomic DNA from the test individual is obtained, and the connexin-32 gene (or a fragment thereof) is amplified. The amplified connexin-32 gene or gene fragment is dot-blotted, and is then contacted with an allele-specific oligonucleotide designed to distinguish single nucleotide alterations in the connexin-32 gene. The presence of a mutation in the connexin-32 gene is identified by hybridization of the allele-specific oligonucleotide to the amplified connexin-32 gene or gene fragment. The presence of a mutation, as described above, in the connexin-32 gene of the individual is indicative of the CMTX disease.

The invention further pertains to mutant connexin-32 nucleic acid probes having at least one of the specific mutations described above. The invention also includes mutant connexin-32 proteins encoded by the mutant connexin-32 nucleic acid probes, as well as antibodies specific for the mutant connexin-32 proteins. The mutant connexin-32 nucleic acid probes, mutant connexin-32 proteins, antibodies to the mutant connexin-32 proteins, and the methods described herein, facilitate identification of mutations in the connexin-32 gene which are associated with X-linked CMT disease, and thereby facilitate diagnosis of the disease. Identification of such mutations distinguishes X-linked disease from other forms of CMT disease, thereby enabling better treatment planning for affected individuals, as well as for other family members which may be affected individuals or disease carriers.

BRIEF DESCRIPTION OF THE FIGURES

FIG. 1A-1B depict the nucleic acid sequence (SEQ ID No. 1) and amino acid sequence (SEQ ID No. 2) of the connexin-32 cDNA and its encoded protein.

DETAILED DESCRIPTION OF THE INVENTION

The current invention relates to certain previously unidentified mutations in the connexin-32 gene. As described in the Example, certain mutations in the connexin-32 gene have been identified in individuals whose clinical presentation was consistent with the diagnosis of CMT disease. It is highly probable that these mutations are associated with X-linked CMT disease, because they were identified in individuals affected by X-linked CMT disease, and because the type of mutations (point mutations, frame shift mutations, deletions) are the same type of mutations as other previously identified mutations associated with X-linked CMT disease (Bergoffen et al. (1993), *Science* 262:2039-2042; Bone et al. (1995), *Neurology* 45:1863-1866; Fairweather et al. (1994), *Hum. Mol. Genet.* 3:29-34; Ionasescu et al. (1994), *Hum. Mol. Genet.* 3:355-358; Tan and Ainsworth (1994), *Am. J. Hum. Genet.* 55(suppl):1431; Cherryson et al. (1994), *Am. J. Hum. Genet.* 55(suppl):1261; Ionasescu (1995), *Muscle & Nerve* 18:267-275; Janssen (in preparation); Tan, C. C. et al. (1996), *Human Mutation* 7:167-171).

As a result of the discovery of these mutations, methods for diagnosing X-linked CMT disease are now available. Diagnosis is made by detecting mutations in the connexin-32 gene that are associated with X-linked CMT disease. A "mutation in the connexin-32 gene", as used herein, refers to a mutation in the gene as well as to a mutation in the cDNA of the gene. "Mutations associated with X-linked CMT disease", as described herein, include mutations in certain codons of the connexin-32 gene. The term "codon" indicates a group of three nucleotides which designate a single amino acid in the gene. The codons are numbered from the beginning of the coding sequence of the protein: the first three nucleotides which together designate the initial methionine residue in the protein, together are "codon 1". The connexin-32 gene has 284 codons, flanked by non-encoding nucleotides. The nucleic acid sequence (SEQ ID NO. 1) of the connexin-32 gene (Kumar, N. M and N. B. Gilula (1986), *J. Cell Biol.* 103:767-776), with portions of the flanking sequence, is shown in the Figure. The amino acid encoded by each codon is indicated below the codon.

Mutations associated with X-linked CMT disease include any mutations in the following codons of the connexin-32 gene: 26, 28, 44, 86, 100, 103, 107, 124, 154, 157, 160, 161, 179, 181, 183, 187, 198, 204, 205, 219, 230 and 235. The mutation can be the addition or subtraction of a single nucleotide in the codon, resulting in a frame shift mutation; the change of at least one nucleotide in the codon, resulting in a change in the amino acid encoded by the codon; the change of at least one nucleotide in the codon, resulting in a change of the codon to a stop codon; the deletion of all three nucleotides in the codon, resulting in a deletion of the amino acid encoded by the codon; or the change of at least one nucleotide in the codon, resulting in a synonymous codon mutation,, in any of the above codons. Mutations associated with X-linked CMT disease also include certain specific mutations in the above-identified codons, as set forth in Table 1, below.

TABLE 1

| Specific Mutations Associated with X-Linked CMT | | |
|---|---|---|
| Codon | Mutation | Amino Acid Change |
| 26 | TCG—>TTG | Ser—>Leu |
| 28 | ATC—>AAC | Ile—>Asn |
| 44 | TGG—>TTG | Trp—>Leu |
| 86 | ACC—>TCC | Thr—>Ser |
| 100 | CAC—>TAC | His—>Tyr |
| 103 | AAG—>GAG | Lys—>Glu |
| 107 | CGG—>TGG | Arg—>Trp |
| 124 | AAG—>AG | Frame shift |
| 154 | TAT—>TAA | Tyr—>STOP codon |
| 157 | TAC—>TGC | Tyr—>Cys |
| 160 | TAT—>CAT | Tyr—>His |
| 161 | GCC—>GCT | (NONE) |
| 179 | TGC—>CGC | Cys—>Arg |
| 181 | GTG—>ATG | Val—>Met |
| 183 | CGC—>TGC | Arg—>Cys |
| 187 | AAA—>GAA | Lys—>Glu |
| 198 | TCT—>TTT | Ser—>Phe |
| 204 | CTC—>GTC | Leu—>Val |
| 205 | AAT—>AGT | Asn—>Ser |
| 219 | CGC—>TGC | Arg—>Cys |
| 230 | CGC—>TGC | Arg—>Cys |
| 235 | TTC—>TGC | Phe—>Cys |

Mutations associated with X-linked CMT disease also include certain specific mutations in codons 12, 75, 142, 172 or 185. These specific mutations are set forth in Table 2, below.

TABLE 2

Additional Specific Mutations Associated with X-Linked CMT

| Codon | Mutation | Amino Acid Change |
|-------|----------|-------------------|
| 12 | GGC—>GGT | (NONE) |
| 75 | CGG—>TGG | Arg—>Trp |
| 142 | CGG—>CAG | Arg—>Glu |
| 172 | CCC—>CTC | Pro—>Leu |
| 185 | ACC deleted | Thr deleted |

In a first method of diagnosing X-linked CMT disease, hybridization methods, such as Southern analysis, are used (see *Current Protocols in Molecular Biology*, Ausubel, F. et al., eds., John Wiley & Sons, 1995). For example, a test sample of genomic DNA is obtained from an individual suspected of having (or carrying a defect for) X-linked CMT disease (the "test individual"). The test sample can be from any source which contains genomic DNA, such as a blood or tissue sample. In a preferred embodiment, the test sample of DNA is obtained from a blood sample. In another preferred embodiment, the test sample of DNA is obtained from buccal cells. The DNA sample is examined to determine whether a mutation associated with X-linked CMT disease is present; the presence of the mutation is indicated by hybridization of the connexin-32 gene in the genomic DNA to a mutant connexin-32 nucleic acid probe. A "mutant connexin-32 nucleic acid probe", as used herein, is a cDNA of the connexin-32 gene which has at least one of the mutations associated with X-linked CMT disease described above (i.e., any mutation in codon 26, 28, 44, 86, 100, 103, 107, 154, 157, 160, 161, 179, 181, 183, 187, 198, 204, 205, 219, 230 or 235, or any one of the specific mutations set forth in Table 1 or Table 2). A fragment of such a mutant connexin-nucleic acid probe can also be used, provided that the fragment contains the mutation. Alternatively, RNA encoded by such a probe can also be used.

To diagnose X-linked CMT disease by hybridization, a hybridization sample is formed by contacting the test sample containing a connexin-32 gene with at least one mutant connexin-32 nucleic acid probe. The hybridization sample is maintained under conditions which are sufficient to allow specific hybridization of the mutant connexin-32 nucleic acid probe to the connexin-32 gene of interest. "Specific hybridization", as used herein, indicates exact hybridization (i.e., with no mismatches). Specific hybridization, if present, is then detected using standard methods. If specific hybridization occurs between the mutant connexin-32 nucleic acid probe and the connexin-32 gene of interest, then the connexin-32 gene of interest has a mutation. The mutation in the connexin-32 gene of interest identified by this method is the same mutation as that present in the mutant connexin-32 nucleic acid probe. More than one mutant connexin-32 nucleic acid probe can also be used concurrently in this method. Specific hybridization of any one of the mutant connexin-32 nucleic acid probes is indicative of a mutation in the connexin-32 gene that is associated with CMTX disease, and is therefore diagnostic for the disease.

In another hybridization method, Northern analysis (see *Current Protocols in Molecular Biology*, Ausubel, F. et al., eds., John Wiley & Sons, 1995) is used to diagnose X-linked CMT disease. For Northern analysis, a sample of RNA is obtained from the test individual. Specific hybridization of a mutant connexin-32 nucleic acid probe, as described above, to RNA from the individual is indicative of a mutation in the connexin-32 gene that is associated with CMTX disease, and is therefore diagnostic for the disease.

In another embodiment of the invention, mutation analysis by restriction digestion can be used to detect a mutation in the connexin-32 gene, if the mutation in the connexin-32 gene results in the creation or elimination of a restriction site. For example, a test sample containing genomic DNA is obtained from the test individual. After digestion of the genomic DNA with an appropriate restriction enzyme, DNA fragments are separated using standard methods, and contacted with a probe containing the connexin-32 gene or cDNA. The digestion pattern of the DNA fragments indicates the presence or absence of the mutation associated with CMTX disease. Alternatively, polymerase chain reaction (PCR) can be used to amplify the connexin-32 gene of interest (and, if necessary, the flanking sequences) in a test sample of genomic DNA from the test individual. Direct mutation analysis by restriction digestion is then conducted as described (Fairweather, N. et al., *Hum. Mol. Genet.* 3(1):29–34 (1994); and Ionasescu, V. et al., *Hum. Mol. Genet.* 3(2):355–358 1994)). The digestion pattern of the relevant DNA fragment indicates the presence or absence of the mutation associated with CMTX disease.

Sequence analysis can also be used to detect specific mutations in the connexin-32 gene, as described (Bergoffen et al. (1993), *Science* 262:2039–2042; Ionasescu, V. et al. (1995), *Neuromuscl. Disord.* 5(4):297–299; Bone et al. (1995), *Neurology* 45:1863–1866). A test sample of DNA is obtained from the test individual. PCR can be used to amplify the connexin-32 gene, and its flanking sequences. The sequence of the connexin-32 gene that is present in the test sample (referred to herein as the "connexin-32 gene of interest"), or a fragment of the gene, is determined, using standard methods. The sequence of the connexin-32 gene (or gene fragment) is compared with the known connexin-32 nucleic acid sequence (SEQ ID NO. 1). The presence of any of the mutations associated with X-linked CMT disease, as described above, indicates that the individual is affected with X-linked CMT disease.

Allele-specific oligonucleotides can also be used to detect the presence of a mutation associated with CMTX disease, through the use of dot-blot hybridization of amplified gene products with allele-specific oligonucleotide (ASO) probes (Saiki, R. et al. (1986), *Nature (London)* 324:163–166; Emi, M. et al. (1988), *Genomic* 3:373–379). An "allele-specific oligonucleotide" (also referred to herein as an "allele-specific oligonucleotide probe") is an oligonucleotide of approximately 10–50 base pairs, preferably approximately 15–30 base pairs, that specifically hybridizes to a connexin-32 gene (or gene fragment) that contains a particular mutation. An allele-specific oligonucleotide probe that is specific for particular mutations in the connexin-32 gene can be prepared, using standard methods (see *Current Protocols in Molecular Biology*, Ausubel, F. et al., eds., John Wiley & Sons, 1995). To identify mutations in the connexin-32 gene associated with CMTX disease, a test sample of DNA is obtained from the test individual. PCR can be used to amplify all or a fragment of the connexin-32 gene, and its flanking sequences. The DNA containing the amplified connexin-32 gene (or fragment of the gene) is dot-blotted, using standard methods (see *Current Protocols in Molecular Biology*, Ausubel, F. et al., eds., John Wiley & Sons, 1995), and the blot is contacted with the oligonucleotide probe. The presence of specific hybridization of the probe to the amplified connexin-32 gene is then detected. Specific hybridization of an allele-specific oligonucleotide probe to DNA from the individual is indicative of a mutation in the connexin-32 gene that is associated with CMTX disease, and is therefore diagnostic for the disease.

The invention also includes isolated, mutant connexin-32 proteins. Mutant connexin-32 proteins are connexin-32 proteins encoded by a connexin-32 gene having at least one of the mutations associated with X-linked CMT disease, as described above. An "isolated" mutant connexin-32 protein, as referred to herein, is a mutant connexin-32 protein that has been separated from the original environment in which it naturally occurs. The current additionally pertains to antibodies which specifically bind to mutant connexin-32 proteins. All or a fragment of a mutant connexin-32 protein can be used to generate antibodies, provided that the mutant connexin-32 protein fragment contains the mutation. The term "antibody", as used herein, encompasses both polyclonal and monoclonal antibodies, as well as mixtures of more than one antibody reactive with a mutant connexin-32 protein or mutant connexin-32 protein fragment (e.g., a cocktail of different types of monoclonal antibodies reactive with the mutant protein or protein fragment). The term antibody is further intended to encompass whole antibodies and/or biologically functional fragments thereof, chimeric antibodies comprising portions from more than one species, humanized antibodies, human-like antibodies, and bifunctional antibodies. Biologically functional antibody fragments which can be used are those fragments sufficient for binding of the antibody fragment to the mutant connexin-32 protein or mutant connexin-32 protein fragment.

The invention is further illustrated by the following Example.

EXAMPLE

Identification of Mutations in the Connexin-32 Gene in Individuals Having Clinical Presentation Consistent with Diagnosis of CMT Disease Mutations in the connexin-32 gene were identified in individuals who were suspected of being affected by CMT disease. Whole blood samples were taken, and white blood cells were isolated. Fifteen ml of whole blood was transferred into 50 ml disposable, sterile, screw-cap conical polypropylene tubes. Cold $NH_4HCO_3$ lysis buffer (140 mM $NH_4Cl$, 10 mM $NH_4HCO_3$) was added to a total volume of 50 ml, and the sample was mixed by inversion. Red blood cells in the sample were allowed to lyse for approximately 5 minutes at room temperature. The samples were then centrifuged for 20 minutes. The lysate was aspirated or pipetted out. The white blood cell (WBC) pellet at the bottom of the tube was washed by resuspending into 10 ml of lysis buffer. After resuspension, the volume was brought up to 50 ml total with lysis buffer, and the resuspended WBC were centrifuged for 20 minutes. The supernatant was aspirated or pipetted out, and the second WBC pellet was either stored at −20° C. or processed for DNA extraction.

Genomic DNA was extracted as follows: the WBC pellet was resuspended in 1X STE (100 mM Nacl, 10 mM Tris, 1 mM EDTA) to a final total volume of 10 ml. 500 ul Proteinase K (1 mg/ml) was added, and the solution was mixed gently. Subsequently, 500 ul 10% SDS was added dropwise while swirling sample. The solution was then capped and placed in a 37° C. water bath, without shaking, for overnight. The DNA was extracted using automated nucleic acid extraction, using an Applied Biosystems 341 nucleic acid purification system. DNA pellets were resuspended with approximately 200 ul TE pH 8.0 (10 mM Tris, 1 mM EDTA), and placed on a rotator overnight to gain a uniform DNA solution.

Genomic DNA was quantified using ultraviolet absorbance, using a Beckman Spectrophotometer. Five ul of dissolved DNA was added to 995 ul water in a 1.5 ml microfuge tube and vortex. The sample was allowed to dissolve for at least 40 minutes with intermittent mixing before reading. The purity of the DNA preparation was estimated, and the DNA concentration was calculated.

After quantitation of DNA in the samples, 10 µg of all samples were diluted to a final concentration of 50 ng/µl. The diluted samples were used to set up polymerase chain reaction (PCR) amplification reactions.

The polymerase chain reaction (PCR) and two sets of oligonucleotide primers were used to amplify the connexin-32 gene in the sample of genomic DNA. The primers are shown in Table 3.

TABLE 3

PCR Amplification Primers

| Primer | Sequence* | Position in Cx-32 | SEQ ID |
|---|---|---|---|
| #F1 | TGA GGC AGG ATG AAC TGG ACA GGT | 54–77 | 3 |
| #R1 | TTG CTG GTG AGC CAC GTG CAT GGC | 334–357 | 4 |
| #F2 | ATC TCC CAT GTG CGG CTG TGG TCC | 273–296 | 5 |
| #R3 | TGG CAG GTT GCC TGG TAT GT | 919–938 | 6 |

*Sequences are shown in the 5'-3' orientation.

PCR reaction mix components for amplification with the first primer set (CMTX #F1 SEQ ID NO: 3 and CMTX #R1 SEQ ID NO: 4) were as follows: 63 ul water (Sigma); 10 ul of PCR Buffer II (stock concentration 10X, giving a reaction tube concentration of 1X) (Perkin-Elmer Cetus); 6 ul of $MgCl_2$ (stock concentration 25 mM, giving a tube concentration of 1.5 mM); 16 ul of nucleotide mixture giving 200 µM tube concentration of each of dATP, dCTP, dGTP, and dTTP (Perkin-Elmer Cetus "Gene Amp dNTPs"); 0.28 ul of each of the primers (stock concentration 50 µM, giving a tube concentration 100 ng/rxn); and 0.5 ul Taq polymerase (stock concentration 5 units/µl, giving a tube concentration of 2.5 units µl ) (Perkin-Elmer Cetus). Order of adding the components followed the sequence stated above. The total volume for the PCR reaction was 100 ul, which included 4 ul of DNA at 50 ng/ul. Amplification conditions for the first primer set (F1/R1) SEQ ID NOS: 3 and 4 were as follows: one cycle of denaturing for 7 minutes at 94° C.; 35 cycles of amplification (denaturing for 30 seconds at 94° C., annealing for 30 seconds at 65° C., and extension for 30 seconds at 72° C.); and one cycle for 10 minutes at 72° C. Amplified samples remained at 4° C. until the Thermocycler was turned off. Amplification using primer set CMTX #F1 SEQ ID NO: 3 and CMTX #R1 SEQ ID NO: 4 yielded a 306 base pair product.

PCR reaction mix components for amplification with the second primer set (CMTX #F2 SEQ ID NO: 5 and CMTX #R3 SEQ ID NO: 6) were: 65 ul water (Sigma); 10 ul of PCR Buffer II (stock concentration 10X, giving a reaction tube concentration of 1X) (Stratagene); 4 ul of $MgCl_2$ (stock concentration 25 mM, giving a tube concentration of 1.0 mM); 16 ul of nucleotide mixture, giving 200 µM tube concentration of each of dATP, dCTP, dGTP, and dTTP (Perkin-Elmer Cetus "Gene Amp dNTPs"); 0.27 ul of primer F2 (SEQ ID NO: 5) (stock concentration 50 µM, giving a tube concentration 100 ng/rxn); 0.33 ul of primer R3 (SEQ ID NO: 6) (stock concentration 50 µM, giving a tube concentration 100 ng/rxn); and 0.5 ul Taq plus polymerase (stock concentration 5 units/µl, giving a tube concentration of 2.5 units µl ) (Stratagene). Order of adding the components followed the sequence stated above. The total volume for the PCR reaction was 100 ul, which included 4 ul of DNA at 50 ng/ul. Amplification conditions for the second primer set (F2/R3) (SEQ ID NOS: 5 and 6) were as follows: one cycle of denaturing for 5 minutes at 94° C.; 35 cycles of amplification (denaturing for one minute at 94° C. annealing for one minute at 63° C, and extension for one minute at 72° C.); and one cycle for 10 minutes at 72° C. Amplified samples remained at 4° C. until the Thermocycler was turned off. Amplification with primer set CMTX #F2 SEQ ID NO: 5 and CMTX #R3 SEQ ID NO: 6 yielded a 666 base pair product.

The amplification products were purified using Qiagen columns, and a QIAquickPCR Purification Kit (QIAGEN Inc., Chatsworth, Calif.). Purified amplification products were then used for sequencing reactions. The sequencing primers are shown in Table 4.

TABLE 4

Sequencing Primers

| Primer | Sequence* | Position in Cx-32 | SEQ ID |
|---|---|---|---|
| #F1 | TGA GGC AGG ATG AAC TGG ACA GGT | 54–77 | 3 |
| #R1 | TTG CTG GTG AGC CAC GTG CAT GGC | 334–357 | 4 |
| #F2 | ATC TCC CAT GTG CGG CTG TGG TCC | 273–296 | 5 |
| #R2 | GAT GAT GAG GTA CAC CAC CT | 685–704 | 7 |
| #F3 | CC GTC TTC ATG CTA GCT GCC TCT GG | 625–658 | 8 |
| #R3 | TGG CAG GTT GCC TGG TAT GT | 917–936 | 6 |

*Sequences are shown in the 5'-3' orientation.

The entire open reading frame was sequenced in the forward and reverse directions using three forward and three reverse sequencing primers for cycle sequencing. A separate tube was used for each sequencing primer. One of two protocols was used, depending on the enzyme involved.

For cycle sequencing with AmpliTaq, labelled reaction tubes (0.5 ml capacity) were filled with a mixture of the following reagents in the order specified: 8.75 ul (F1 SEQ ID NO: 3 or R1 SEQ ID NO: 4) or 8.90 ul (F2, SEQ ID NO: 5 R2, SEQ ID NO: 7 F3, SEQ ID NO: 8or R3 SEQ ID NO: 6) of water (Sigma); 1.0 ul primer (stock concentration 50 µM), described above; 0.75 ul template DNA for F1 SEQ ID NO: 3 and R1, SEQ ID NO: 4 and 0.60ul template DNA for F2, SEQ ID NO: 5 R2, SEQ ID NO: 7, F3 SEQ ID NO: 8 and R3 SEQ ID NO: 6; and 9.5 ul terminator pre-mix containing Enzyme (ABI PRISM™ Dye Terminator Cycle Sequencing Ready Reaction Kit with AmpliTaq DNA Polymerase).

Alternatively, FS Amplitaq was used. For cycle sequencing with FS AmpliTaq, labelled reaction tubes (0.5 ml capacity) were filled with a mixture of the following reagents in the order specified: 11.14 ul (F1 SEQ ID NO: 3, F2 SEQ ID NO: 5, R2 SEQ ID NO: 7, F3 SEQ ID. NO: 8, R3 SEQ ID NO: 6) or 11.9 ul (R1 SEQ ID NO: 4) of water (Sigma); 0.5 ul primer (stock concentration 50 µM), described above; 0.36 ul template DNA for F1 SEQ ID NO: 3, F2 SEQ ID NO: 5, R2 SEQ ID NO: 7, F3 SEQ ID NO: 8, and R3 SEQ ID NO: 6, and 0.60 ul template DNA for R1 SEQ ID NO: 4, and 8.0 ul terminator pre-mix containing FS Enzyme (ABI PRISM™ Dye Terminator Cycle Sequencing Ready Reaction Kit with AmpliTaq DNA Polymerase, FS).

For either AmpliTaq or FS AmpliTaq, each reaction mixture was overlaid with 20 ul of mineral oil, and the tubes were capped tightly. The tubes were placed in a Thermocycler (TC-480 Thermocycler (Perkin-Elmer Cetus). Cycle sequencing was performed for 25 cycles. For the 306 bp fragment, cycle sequencing was conducted under the following conditions: denaturing for 30 seconds at 96° C.; annealing for 15 seconds at 50° C.; and extension for four minutes at 60° C. For the 666 bp fragment, cycle sequencing was conducted under the following conditions: denaturing for 30 seconds at 96° C.; annealing for 15 seconds at 60° C.; and extension for four minutes at 60° C. After the last cycle, samples remained at 4° C. until the Thermocycler was turned off.

Cycle sequenced products were then separated on an ABI 373 automated sequencer (ABI), and the results were analyzed using Factura™ Version 1.2.0 and Sequence navigator™ version 1.0.1 software programs (ABI).

For quality control, positive control samples from three male/female individuals known to have a point mutation in each of the three fragments of the connexin-32 coding regions (i.e., the fragments generated by the F1/R1 SEQ ID NOS: 3 and 4, F2/R2 SEQ ID NO:5, and F3/R3 SEQ ID NOS: 8 and 6 primers) were used. Using this method, 27 previously unknown mutations in the connexin-32 gene were identified. The mutations are set forth in Table 5, below. Column 2 of Table 5 identifies whether the mutation was found in the connexin-32 gene of a male or of a female individual.

TABLE 5

New Mutations in the Connexin-32 Gene

| Sample | Male/ Female | Mutation Detected | Codon Affected | Amino Acid Change |
|---|---|---|---|---|
| 1 | Male | AAA—>GAA | 187 | Lys—>Glu |
| 2 | Male | AAG—>AG | 124 | Frame shift |
| 3 | Female | GTG—>ATG | 181 | Val—>Met |
| 4 | Male | CGC—>TGC | 183 | Arg—>Cys |
| 5 | Male | AAT—>AGT | 205 | Asn—>Ser |
| 6 | Male and Female | CAC—>TAC | 100 | His—>Tyr |
| 7 | Male | TAT—>TAA | 154 | Tyr—>STOP |
| 8 | Male | CGG—>TGG | 107 | Arg—>Trp |
| 9 | Female | AAG—>GAG | 103 | Lys—>Glu |
| 10 | Male | CGG—>TGG | 75 | Arg—>Trp |
| 11 | Female | GCC—>GCT | 161 | None |
| 12 | Female | GGC—>GGT | 12 | None |
| 13 | Male | TGC—>CGC | 179 | Cys—>Arg |
| 14 | Male | TAC—>TGC | 157 | Try—>Cys |
| 15 | Female | CTC—>GTC | 204 | Leu—>Val |
| 16 | Male | TCT—>TTT | 198 | Ser—>Phe |
| 17 | Male | ACC deleted | 185 | Thr deleted |
| 18 | Male | CGC—>TGC | 219 | Arg—>Cys |
| 19 | Female | CGC—>TGC | 230 | Arg—>Cys |
| 20 | Male | TGG—>TTG | 44 | Trp—>Leu |
| 21 | Female | TAT—>CAT | 160 | Tyr—>His |
| 22 | Male | CCC—>CTC | 172 | Pro—>Leu |
| 23 | Female | CGG—>CAG | 142 | Arg—>Glu |
| 24 | Male | TCG—>TTG | 26 | Ser—>Leu |
| 25 | Female | ACC—>TCC | 86 | Thr—>Ser |
| 26 | Male | ATC—>AAC | 28 | Ile—>Asn |
| 27 | Female | TTC—>TGC | 235 | Phe—>Cys |

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of diagnosing X-linked Charcot-Marie-Tooth disease in an individual, comprising detecting a mutation in the connexin-32 gene of the individual, the mutation being in at least one codon selected from the group consisting of: 28, 44, 86, 100, 103, 124, 154, 157, 160, 161, 179, 181, 183, 187, 198, 204, 205, 219, 230 and 235, wherein the presence of the mutation in the connexin-32 gene is indicative of X-linked Charcot-Marie-Tooth disease.

2. A method of diagnosing X-linked Charcot-Marie-Tooth disease in an individual, comprising detecting the presence of a mutation in the connexin-32 gene of the individual, the mutation being selected from the group consisting of:

a change in the nucleic acid sequence of codon 12 from GGC to GGT;

a change in the nucleic acid sequence of codon 28 from ATC to AAC;

a change in the nucleic acid sequence of codon 44 from TGG to TTG;

a change in the nucleic acid sequence of codon 75 from CGG to TGG;

a change in the nucleic acid sequence of codon 86 from ACC to TCC;

a change in the nucleic acid sequence of codon 100 from CAC to TAC;

a change in the nucleic acid sequence of codon 103 from AAG to GAG;

a change in the nucleic acid sequence of codon 124 from AAG to AG;

a change in the nucleic acid sequence of codon 142 from CGG to CAG;

a change in the nucleic acid sequence of codon 154 from TAT to TAA;

a change in the nucleic acid sequence of codon 157 from TAC to TGC;

a change in the nucleic acid sequence of codon 160 from TAT to CAT;

a change in the nucleic acid sequence of codon 161 from GCC to GCT;

a change in the nucleic acid sequence of codon 172 from CCC to CTC;

a change in the nucleic acid sequence of codon 179 from TGC to CGC;

a change in the nucleic acid sequence of codon 181 from GTG to ATG;

a change in the nucleic acid sequence of codon 183 from CGC to TGC;

a deletion of codon 185;

a change in the nucleic acid sequence of codon 187 from AAA to GAA;

a change in the nucleic acid sequence of codon 198 from TCT to TTT;

a change in the nucleic acid sequence of codon 204 from CTC to GTC;

a change in the nucleic acid sequence of codon 205 from AAT to AGT;

a change in the nucleic acid sequence of codon 219 from CGC to TGC;

a change in the nucleic acid sequence of codon 230 from CGC to TGC; and a change in the nucleic acid sequence of codon 235 from TTC to TGC, wherein the presence of a mutation in the connexin-32 gene is indicative of X-linked Charcot-Marie-Tooth disease.

3. A method of diagnosing X-linked Charcot-Marie-Tooth disease in an individual, comprising the steps of:

a. obtaining from the individual a test sample of DNA containing the connexin-32 gene;

b. examining the test sample for the presence of a mutation in the connexin-32 gene, the mutation being in at least one codon selected from the group consisting of: 28, 44, 86, 100, 103, 124, 154, 157, 160, 161, 179, 181, 183, 187, 198, 204, 205, 219, 230 and 235, wherein the presence of the mutation in the connexin-32 gene is indicative of X-linked Charcot-Marie-Tooth disease.

4. The method of claim 3, wherein the presence of the mutation in the connexin-32 gene is detected by direct mutation analysis by restriction digestion.

5. The method of claim 3, wherein the presence of the mutation in the connexin-32 gene is detected by hybridization of a mutant connexin-32 nucleic acid probe to the connexin-32 gene in the test sample.

6. The method of claim 3, wherein the presence of the mutation in the connexin-32 gene is detected by sequence analysis of the connexin-32 gene.

7. The method of claim 3, wherein the presence of the mutation in the connexin-32 gene is detected by hybridization of an allele-specific oligonucleotide with the connexin-32 gene in the test sample.

8. A method of diagnosing X-linked Charcot-Marie-Tooth disease in an individual, comprising the steps of:

a. obtaining from the individual a test sample of DNA containing the connexin-32 gene;

b. examining the test sample for the presence of a mutation in the connexin-32 gene, the mutation being selected from the group consisting of:

a change in the nucleic acid sequence of codon 12 from GGC to GGT;

a change in the nucleic acid sequence of codon 28 from ATC to AAC;

a change in the nucleic acid sequence of codon 44 from TGG to TTG;

a change in the nucleic acid sequence of codon 75 from CGG to TGG;

a change in the nucleic acid sequence of codon 86 from ACC to TCC;

a change in the nucleic acid sequence of codon 100 from CAC to TAC;

a change in the nucleic acid sequence of codon 103 from AAG to GAG;

a change in the nucleic acid sequence of codon 124 from AAG to AG;

a change in the nucleic acid sequence of codon 142 from CGG to CAG;

a change in the nucleic acid sequence of codon 154 from TAT to TAA;

a change in the nucleic acid sequence of codon 157 from TAC to TGC;

a change in the nucleic acid sequence of codon 160 from TAT to CAT;

a change in the nucleic acid sequence of codon 161 from GCC to GCT;

a change in the nucleic acid sequence of codon 172 from CCC to CTC;

a change in the nucleic acid sequence of codon 179 from TGC to CGC;

a change in the nucleic acid sequence of codon 181 from GTG to ATG;

a change in the nucleic acid sequence of codon 183 from CGC to TGC;

a deletion of codon 185;

a change in the nucleic acid sequence of codon 187 from AAA to GAA;

a change in the nucleic acid sequence of codon 198 from TCT to TTT;

a change in the nucleic acid sequence of codon 204 from CTC to GTC;

a change in the nucleic acid sequence of codon 205 from AAT to AGT;

a change in the nucleic acid sequence of codon 219 from CGC to TGC;

a change in the nucleic acid sequence of codon 230 from CGC to TGC; and a change in the nucleic acid sequence of codon 235 from TTC to TGC, wherein the presence of a mutation in the connexin-32 gene is indicative of X-linked Charcot-Marie-Tooth disease.

9. The method of claim 8, wherein the presence of the mutation in the connexin-32 gene is detected by direct mutation analysis by restriction digestion.

10. The method of claim 8, wherein the presence of the mutation in the connexin-32 gene is detected by hybridization of a mutant connexin-32 nucleic acid probe to the connexin-32 gene in the test sample.

11. The method of claim 8, wherein the presence of the mutation in the connexin-32 gene is detected by sequence analysis of the connexin-32 gene.

12. The method of claim 8, wherein the presence of the mutation in the connexin-32 gene is detected by hybridization of an allele-specific oligonucleotide with the connexin-32 gene in the test sample.

13. A method of diagnosing X-linked Charcot-Marie-Tooth disease in an individual, comprising the steps of:

a. obtaining from the individual a test sample of DNA comprising the connexin-32 gene of interest;

b. determining the nucleic acid sequence of all or a fragment of the connexin-32 gene of interest; and c. comparing the nucleic acid sequence of the connexin-32 gene of interest or the fragment of the connexin-32 gene of interest to SEQ ID NO. 1, wherein the presence of a mutation in the connexin-32 gene of interest or fragment of the connexin-32 gene of interest, as compared to SEQ ID NO. 1, the mutation being in at least one codon selected from the group consisting of: 28, 44, 86, 100, 103, 124, 154, 157, 160, 161, 179, 181, 183, 187, 198, 203, 205, 219, 230 and 235, is indicative of X-linked Charcot-Marie-Tooth disease.

14. The method of claim 13, wherein the mutation is selected from the group consisting of:

a change in the nucleic acid sequence of codon 28 from ATC to AAC;

a change in the nucleic acid sequence of codon 44 from TGG to TTG;

a change in the nucleic acid sequence of codon 86 from ACC to TCC;

a change in the nucleic acid sequence of codon 100 from CAC to TAC;

a change in the nucleic acid sequence of codon 103 from AAG to GAG;

a change in the nucleic acid sequence of codon 124 from AAG to AG;

a change in the nucleic acid sequence of codon 154 from TAT to TAA;

a change in the nucleic acid sequence of codon 157 from TAC to TGC;

a change in the nucleic acid sequence of codon 160 from TAT to CAT;

a change in the nucleic acid sequence of codon 161 from GCC to GCT;

a change in the nucleic acid sequence of codon 179 from TGC to CGC;

a change in the nucleic acid sequence of codon 181 from GTG to ATG;

a change in the nucleic acid sequence of codon 183 from CGC to TGC;

a change in the nucleic acid sequence of codon 187 from AAA to GAA;

a change in the nucleic acid sequence of codon 198 from TCT to TTT;

a change in the nucleic acid sequence of codon 204 from CTC to GTC;

a change in the nucleic acid sequence of codon 205 from AAT to AGT;

a change in the nucleic acid sequence of codon 219 from CGC to TGC;

a change in the nucleic acid sequence of codon 230 from CGC to TGC; and a change in the nucleic acid sequence of codon 235 from TTC to TGC.

15. A method of diagnosing X-linked Charcot-Marie-Tooth disease in an individual, comprising the steps of:

a. obtaining from the individual a test sample of DNA comprising the connexin-32 gene of interest;

b. determining the nucleic acid sequence of all or a fragment of the connexin-32 gene of interest; and c. comparing the nucleic acid sequence of the connexin-32 gene of interest or the fragment of the connexin-32 gene of interest to SEQ ID NO. 1, wherein the presence of a mutation in the connexin-32 gene of interest or fragment of the connexin-32 gene of interest, as compared to SEQ ID NO. 1, the mutation being in at least one codon selected from the group consisting of:

a change in the nucleic acid sequence of codon 12 from GGC to GGT;

a change in the nucleic acid sequence of codon 75 from CGG to TGG;

a change in the nucleic acid sequence of codon 142 from CGG to CAG;

a change in the nucleic acid sequence of codon 172 from CCC to CTC; and a deletion of codon 185, is indicative of a mutation in the connexin-32 gene that is associated with X-linked Charcot-Marie-Tooth disease.

* * * * *

UNITED STATES PATENT AND TRADEMARK OFFICE
Certificate

Patent No. 5,691,144                                        Patented: November 25, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Michael Alan Boss, Acton, MA; Uma Ananth, Shrewsbury, MA; Kimberley Ottaway, Belmont, MA; and William K. Seltzer, Holden, MA.

Signed and Sealed this Tenth Day of June 2003.

*GARY JONES*
*Supervisory Patent Examiner*
Art Unit 1634